(12) United States Patent
Vogel

(10) Patent No.: US 11,366,008 B2
(45) Date of Patent: Jun. 21, 2022

(54) STAND SCALE WITH REMOVABLE DISPLAY AND CONTROL UNIT

(71) Applicant: SECA GMBH & CO. KG, Hamburg (DE)

(72) Inventor: Frederik Vogel, Hamburg (DE)

(73) Assignee: SECA GMBH & CO. KG, Hamburg (DE)

( * ) Notice: Subject to any disclaimer, the term of this patent is extended or adjusted under 35 U.S.C. 154(b) by 316 days.

(21) Appl. No.: 16/806,551

(22) Filed: Mar. 2, 2020

(65) Prior Publication Data

US 2020/0408589 A1    Dec. 31, 2020

(30) Foreign Application Priority Data

Feb. 19, 2019    (DE) ..................... 10 2019 104 165.1

(51) Int. Cl.
*G01G 19/50* (2006.01)
*A61B 5/107* (2006.01)
*G01G 21/28* (2006.01)
*G01G 23/37* (2006.01)

(52) U.S. Cl.
CPC .......... *G01G 19/50* (2013.01); *A61B 5/1072* (2013.01); *G01G 21/28* (2013.01); *G01G 23/3728* (2013.01)

(58) Field of Classification Search
CPC .... G01G 21/28; G01G 23/3728; G01G 19/50; A61B 5/1072
See application file for complete search history.

(56) References Cited

U.S. PATENT DOCUMENTS

| | | | | |
|---|---|---|---|---|
| 6,472,617 B1 * | 10/2002 | Montagnino | .......... | G01G 19/50 177/245 |
| 6,590,166 B2 * | 7/2003 | Yoshida | ................. | A61B 5/742 177/245 |
| 9,186,073 B2 * | 11/2015 | Petrucelli | ............... | G16H 40/63 |

* cited by examiner

*Primary Examiner* — Randy W Gibson
(74) *Attorney, Agent, or Firm* — Lucas & Mercanti, LLP; Klaus P. Stoffel

(57) ABSTRACT

An apparatus for measuring the weight of a person, wherein the weight measuring apparatus has at least one digital display and operator control unit. The at least one display and operator control unit is connectable to the weight measuring apparatus in at least two different positions in the region of a top segment thereof, so as to realize improved operability of the apparatus from different sides.

14 Claims, 5 Drawing Sheets

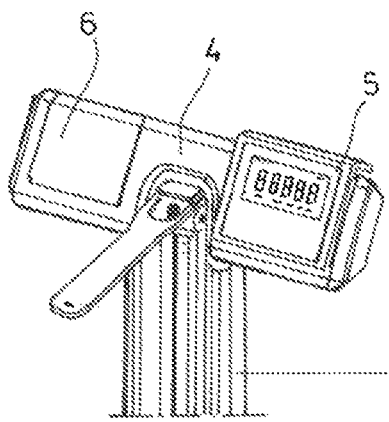
FIG.4.1
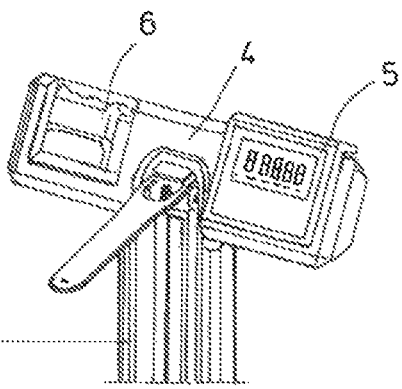
FIG.4.2
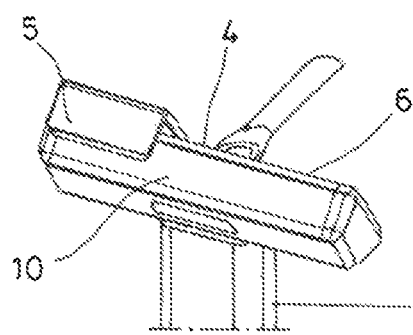
FIG.4.3
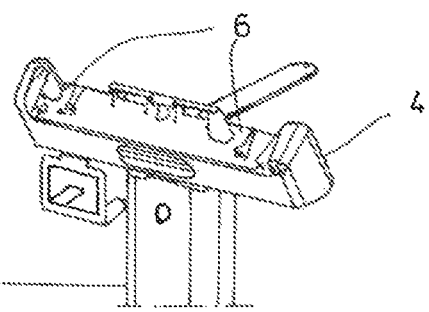
FIG.4.4
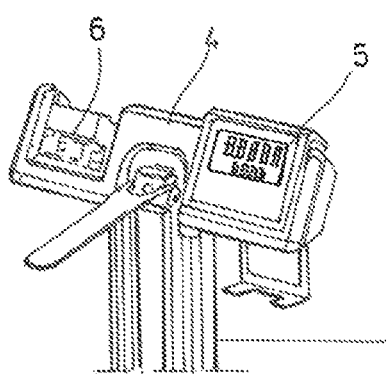
FIG.4.5
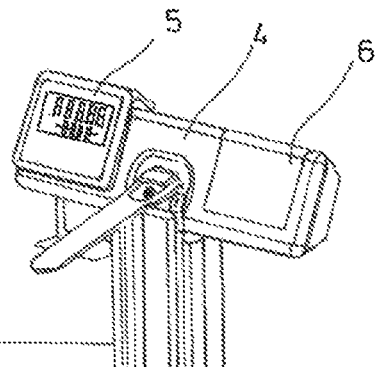
FIG.4.6

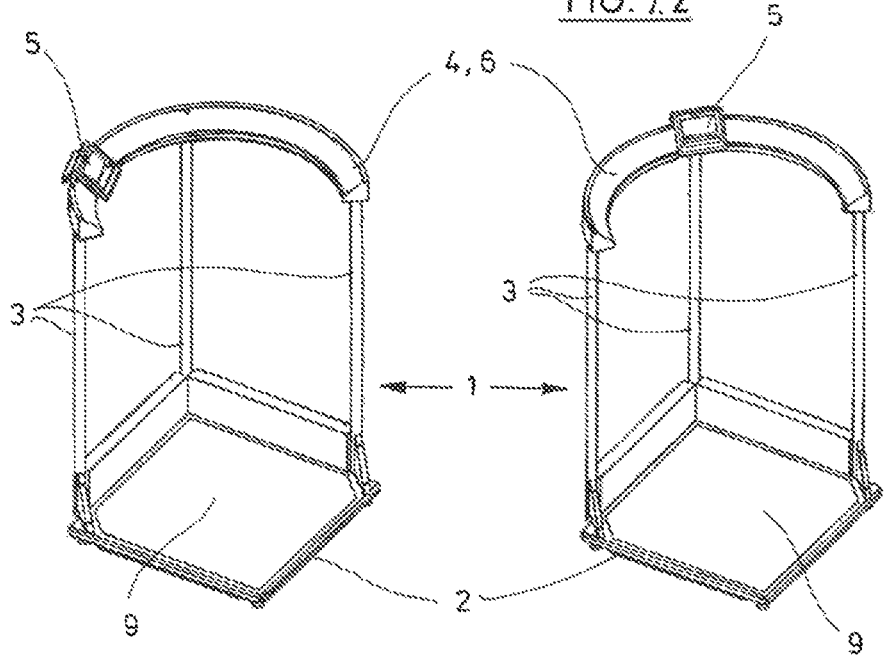
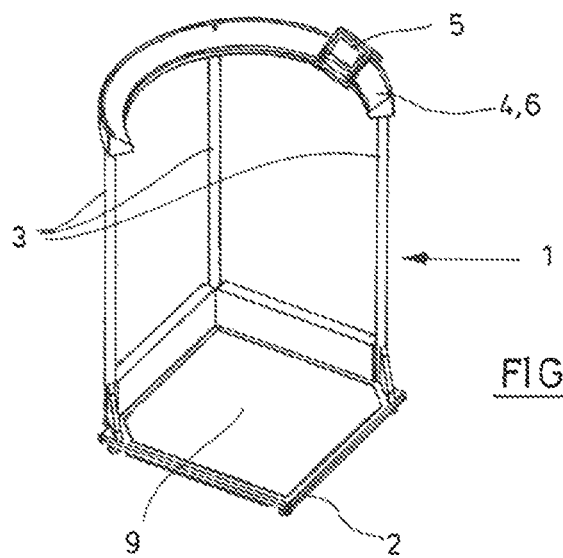

STAND SCALE WITH REMOVABLE DISPLAY AND CONTROL UNIT

CROSS-REFERENCE TO RELATED APPLICATIONS

The present application claims priority of DE 10 2019 104 165.1, filed Feb. 19, 2019, the priority of this application is hereby claimed and this application is incorporated herein by reference.

BACKGROUND OF THE INVENTION

The invention relates to an apparatus for measuring the weight of a person, wherein the weight measuring apparatus has at least one digital display and operator control unit.

Prior art weight measuring apparatuses having a digital display and operator control unit are in the form for example of stand scales and have a base, in the region of which a sensor system for weight recording is arranged, and at least one strut that extends upward from the base and is in the form for example of a pillar. Arranged at the upper end of the strut is a digital display and operator control unit. The digital display and operator control unit is, according to the prior art, factory-positioned in the region of the top segment, either laterally or centrally with respect to the scale, and connected fixedly to the top segment.

Corresponding weight measuring apparatuses, for example stand scales, are relatively large compared with other medical devices that are used in medical practices.

Therefore, medical staff tend to arrange the weight measuring apparatus close to the walls or in the region of corners of the treatment room. This makes it difficult for the medical staff to access the display and operator control unit, since, in addition to the display and operator control unit possibly being arranged on the weight measuring apparatus in an unfavorable manner in relation to the positioning of the weight measuring apparatus in the room, the patient stands on the scale during the measurement and partially conceals the display and operator control unit with their body.

SUMMARY OF THE INVENTION

Therefore, it is an object of the invention to specify an apparatus of the type mentioned at the beginning such that improved accessibility to the display and operator control unit for the medical staff is realized regardless of the positioning of the weight measuring apparatus in the treatment room.

This object is achieved according to the invention in that at least one receiving and connecting device is arranged in the region of the top segment of the weight measuring apparatus, wherein the digital display and operator control unit is connectable to said receiving and connecting device such that it is possible to position the display and operator control unit in at least two different positions in the region of the top segment.

A weight measuring apparatus according to the invention having a digital display and operator control unit comprises some or all of the features mentioned in the following text in all implementable combinations of features.

According to a preferred embodiment of a weight measuring apparatus according to the invention, the latter has a base in which the sensor system required for recording the body weight of a person is arranged.

Arranged on the top side of the base is a weighing surface, on which a person positions themself in order to have their body weight recorded by the weight measuring apparatus.

In one embodiment of the invention, at least one strut that is in the form for example of a pillar is arranged in the region of the base, said strut extending upward in relation to the weighing surface arranged on the top side of the base.

The at least one strut extends preferably from the region of the front side of the base or from a region of the sides of the base that faces the front side of the base.

In a preferred embodiment of the invention, the weight measuring apparatus is in the form of a stand scale.

In one embodiment of a weight measuring apparatus in the form of a stand scale, a strut in the form of a pillar extends perpendicularly upward at the center of the front side of the base in relation to the weighing surface arranged on the top side of the base.

In one preferred embodiment of a weight measuring apparatus according to the invention a top segment that has a substantial horizontal extension component is arranged on the top side of the at least one strut.

In a preferred embodiment of the invention, the top segment extends transversely to the longitudinal direction of the strut.

In a particularly preferred embodiment of the invention, the strut is arranged at the center of the front side of the base and the top segment is arranged on the top side of the strut such that it extends laterally to the left and right on top of the strut. The strut, which is configured in the form of a pillar, and the top segment are configured in a manner connected together in the shape of a hammer in this embodiment.

In a further embodiment of a weight measuring apparatus according to the invention, the latter has one or more struts that extend upward from the region of the base and, by way of a curved shape or by the connection to further strut elements, form a profile that has a horizontal extension component in the region of the top segment.

In a preferred embodiment of the abovementioned weight measuring apparatus, the profile realized with the aid of the at least one strut is embodied in an approximately U-shaped or arcuate manner and either with seamless transitions or in an angular manner, wherein the U-shaped profile opens in the direction of the base.

In one embodiment of the invention, a handrail is realized with the aid of the at least one strut.

In one embodiment of the invention, the handrail is formed as a circular segment at least in the region of the top segment.

A weight measuring apparatus according to the invention has at least one digital display and operator control unit, which is arranged in the region of the top segment. According to the invention, at least one receiving and connecting device is arranged in the region of the top segment, at least one digital display and operator control unit being connectable to said receiving and connecting device in a releasable manner such that it is possible to position the display and operator control unit in at least two different positions in the region of the top segment.

In one embodiment according to the invention of a weight measuring apparatus, for this purpose, two receiving and connecting devices are arranged in at least two fixed positions in the region of the top segment of the weight measuring apparatus, a digital display and operator control unit being connectable to said receiving and connecting devices.

In a preferred embodiment of a weight measuring apparatus, the latter has two receiving and connecting devices in the top segment, of which one receiving and connecting device is arranged in a left-hand region of the top segment and a second receiving and connecting unit is arranged in a right-hand region of the top segment.

In a further embodiment according to the invention of a weight measuring apparatus, the latter has at least one receiving and connecting device in the top segment, said receiving and connecting device extending in the longitudinal direction of the top segment and a digital display and operator control unit being connectable to said receiving and connecting device in different positions.

In a particularly preferred embodiment of a weight measuring apparatus according to the invention having at least one receiving and connecting device extending in the longitudinal direction of the top segment, the digital display and operator control unit is freely connectable to the receiving and connecting device within the extension range of the latter, meaning that, apart from the end positions defined by the external dimensions of the receiving and connecting devices, there are no specified positions for the display and operator control unit in the longitudinal direction of the receiving and connecting device.

In one embodiment according to the invention of a weight measuring apparatus having at least one horizontally extending receiving and connecting device, the latter is in the form of a rail, to which the display and operator control unit is connectable and on which the digital display and operator control unit is freely movable.

In a further embodiment of a weight measuring apparatus according to the invention, the receiving and connecting device in the form of a horizontally extending rail has latching points that define fixed positions for the at least one display and operator control unit in a horizontal direction.

In a further embodiment according to the invention of a weight measuring apparatus, the at least one receiving and connecting device is in the form of a hook-and-loop strip, which extends horizontally in the region of the top segment and to which a digital display and operator control unit is correspondingly connectable by way of a hook-and-loop element configured in a manner corresponding to the hook-and-loop strip.

In a further embodiment of a weight measuring apparatus according to the invention, the at least one receiving and connecting device is in the form of a magnetic strip extending horizontally in the region of the top segment or in the form of a ferromagnetic rail or in the form of magnetic elements that are arranged in a row in a horizontal direction or in the form of ferromagnetic elements that are arranged in a row in a horizontal direction, such that a digital display and operator control unit having a corresponding magnetic or ferromagnetic connecting element is connectable to the receiving and connecting device.

In one embodiment of a weight measuring apparatus according to the invention, receiving and connecting devices that are not connected to a display and operator control unit or regions of a receiving and connecting device that are not connected to a display and operator control unit are closable by one or more covers.

In different embodiments of a weight measuring apparatus according to the invention, the display and operator control unit can be fixed to the at least one receiving and connecting device in the region of the top segment preferably by screwing, magnetic forces, hook-and-loop elements or by the engagement of corresponding latching devices on the display and operator control unit and the at least one receiving and connecting device.

A digital display and operator control unit of a weight measuring apparatus according to the invention has at least one display and at least one input device for recording user inputs.

In one embodiment according to the invention of a weight measuring apparatus, the digital display and operator control unit serves to control the weight measuring apparatus, for example to switch on the measuring device, to start a measurement, to tare the system, to switch between weight units and/or to actuate additional measuring functions. Furthermore, the digital display and operator control unit serves to display measurements and/or the settings selected by the operator.

In one embodiment according to the invention of a weight measuring apparatus, the digital display and operator control unit is connected by cable to the weight measuring apparatus.

In a further embodiment of the invention, the digital display and operator control unit is connected wirelessly to the weight measuring apparatus. Connection of the digital display and operator control unit to the corresponding electronics in the rest of the weight measuring apparatus is in this case embodied preferably as a wireless transmission interface, configured for example as a Wi-Fi or Bluetooth interface.

In one embodiment of the invention, the at least one digital display and operator control unit has an integrated energy store, which is configured preferably as a rechargeable battery.

In one embodiment of a weight measuring apparatus according to the invention, the wireless interface of the digital display and operator control unit is furthermore usable for integrating the weight measuring apparatus in a digital patient system.

In a preferred embodiment, the weight measuring apparatus has at least one additional functional component. The additional functional component is realized for example as a height measuring device, which is preferably in the form of a height rod.

In one embodiment of the invention, the latter has a height measuring device that is vertically positionable.

In one embodiment of a weight measuring apparatus according to the invention, the height rod is arranged in the region of a strut of the weight measuring apparatus. Particularly preferably, the weight measuring apparatus is in this case in the form of a stand scale and the height measuring device is arranged in the region of the pillar.

In one embodiment according to the invention of a weight measuring apparatus, the height rod has a pivotable head piece.

In one embodiment according to the invention of a weight measuring apparatus, a digital height measuring system, with which the height of a person on the scale is able to be determined, is implemented with the aid of the height rod.

In one embodiment according to the invention of a weight measuring apparatus, the measurement, recorded with the aid of the digital height measuring system, of the height of the person is able to be shown on the display of the display and operator control unit.

In one embodiment according to the invention of a weight measuring apparatus, it is additionally possible to read off the height measurement directly from a scale in the region of the height rod.

In one embodiment according to the invention of a weight measuring apparatus, the latter has two digital display and operator control units, which are connected to the top segment in various positions in the region of the latter.

Preferably, these two digital display and operator control units are arranged such that a first digital display and operator control unit is arranged on the side that is accessible from the left-hand side of the weight measuring apparatus and a second digital display and operator control unit is arranged so as to be accessible from the right-hand side of the weight measuring apparatus.

In one embodiment of a weight measuring apparatus according to the invention, the latter has a scanner, with which for example barcodes and/or QR codes for identifying a patient or for recording a patient ID are able to be read.

The various features of novelty which characterize the invention are pointed out with particularity in the claims annexed to and forming a part of the disclosure. For a better understanding of the invention, its operating advantages, specific objects attained by its use, reference should be had to the drawings and descriptive matter in which there are illustrated and described preferred embodiments of the invention.

DETAILED DESCRIPTION OF THE INVENTION

Figure 1:
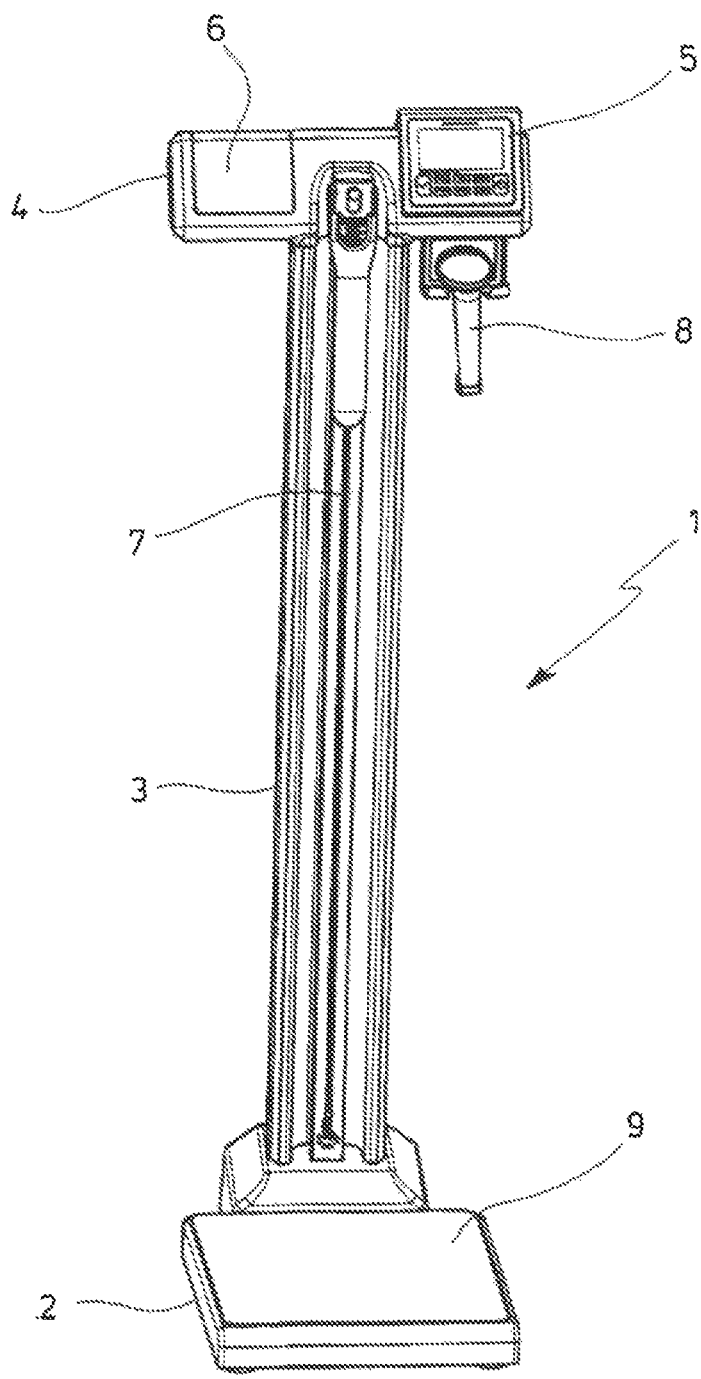
FIG. 1 shows a perspective view of a weight measuring apparatus according to the invention in the form of a stand scale having a digital display and operator control unit connected to a hammer-shaped module made up of a top segment and a pillar.

FIG. 1 shows a perspective view of a weight measuring apparatus (1) according to the invention in the form of a stand scale. The weight measuring apparatus (1) has a base (2), a pillar (3) extending upward from the base, and a top segment (4) arranged at the top end of the pillar (3). The top segment (4) extends transversely to the longitudinal direction of the pillar (3), such that the unit formed by the pillar (3) and the top segment (4) is in the shape of a hammer.

Arranged in the region of the top segment (4) are two receiving and connecting devices (6), of which a first receiving and connecting device (6) is arranged on the left-hand side of the top segment (4) and a second receiving and connecting device (6) is arranged on the right-hand side of the top segment (4).

The receiving and connecting device (6) arranged on the left-hand side of the top segment (4) is closed with the aid of a cover. The receiving and connecting device (6) arranged on the right-hand side of the top segment (4) is connected to a display and operator control unit (5). In the region of the pillar (3) the illustrated embodiment of a weight measuring apparatus (1) according to the invention has a height measuring device (7).

A scanner (8) is mounted beneath the display and operator control unit (5) with the aid of a corresponding mounting device.

A weighing surface (9) is arranged on the top side of the base (2) of the embodiment according to the invention of a weight measuring apparatus (1).

Figure 2:
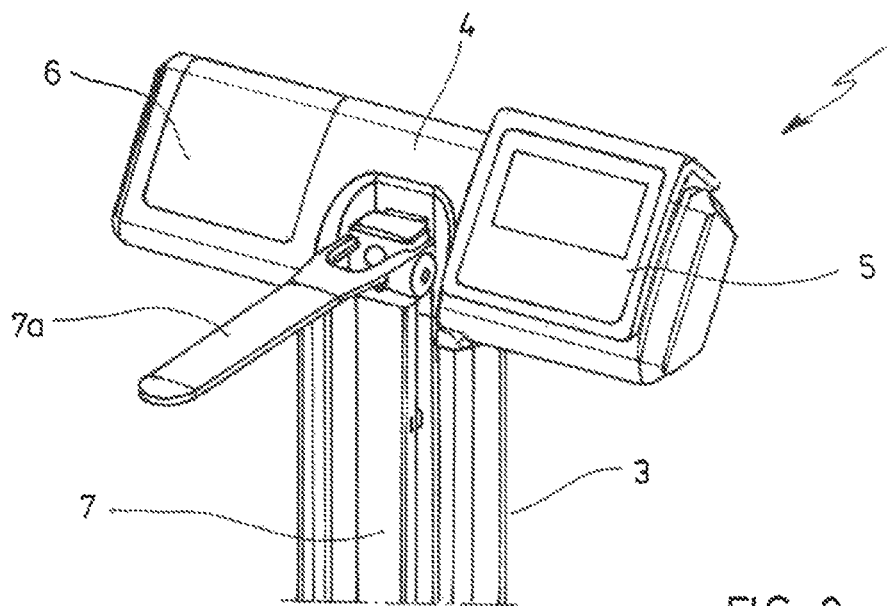
FIG. 2 shows a perspective view of a detail in the top region of the stand scale according to the invention in FIG. 1.

FIG. 2 illustrates a detail of a perspective illustration of the weight measuring apparatus (1) illustrated in FIG. 1 in the region of the top segment (4). Furthermore, the height measuring device (7) of the illustrated embodiment according to the invention of a weight measuring apparatus (1) has a pivotable head piece (7a).

Figure 3:
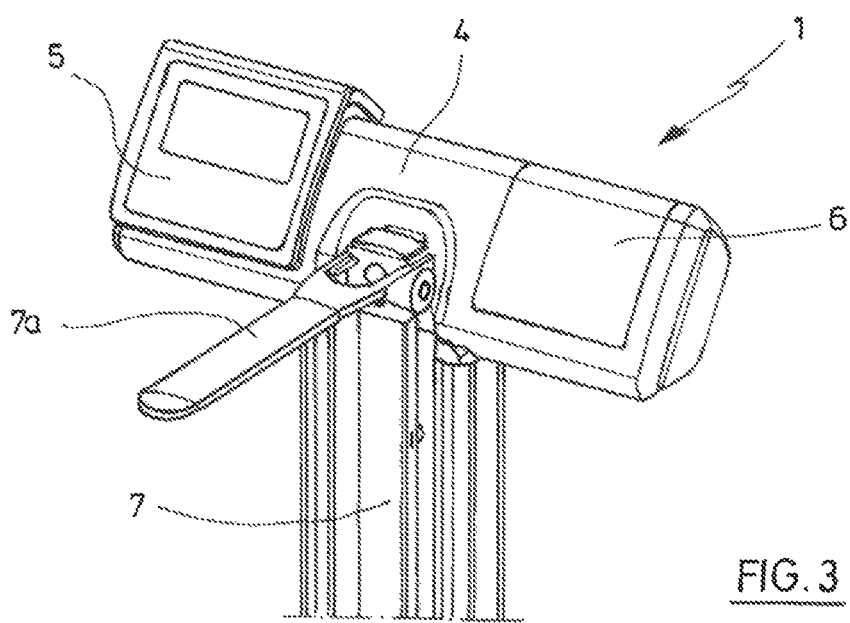
FIG. 3 shows a perspective view of the stand scale illustrated in FIGS. 1 and 2 in a detail of the top region, wherein the digital display and operator control unit is now arranged on the left-hand side of the top segment, FIG. 4.1 shows a perspective view of the detail in the top region of the stand scale illustrated in FIG. 1 in order to illustrate the required steps for changing the positions of the digital display and operator control unit, this figure shows a first step, FIG. 4.2 shows a further step for changing the positions, FIG. 4.3 shows a rear perspective view, FIG. 4.4 shows the view of FIG. 4.3 with a part remover, FIG. 4.5 shows a further step for changing the positions, FIG. 4.6 shows the change completed.

FIG. 3 shows a detail of a perspective view of the weight measuring apparatus (1) illustrated in FIGS. 1 and 2, wherein the display and operator control unit (5) is now connected to the receiving and connecting device (6) on the left-hand side of the top segment (4) and the receiving and connecting device (6) on the right-hand side of the top segment (4) is closed by a cover. While the display and operator control unit (5) of the configuration of a weight measuring apparatus (1) according to the invention illustrated in FIGS. 1 and 2 exhibits increased accessibility from the right-hand side of the weight measuring apparatus (1), this is provided from the left-hand side of the weight measuring apparatus (1) in the configuration of a weight measuring apparatus (1) according to the invention illustrated in FIG. 3.

FIG. 4 shows, in six illustrations, different steps that are necessary for changing the position of the digital display and operator control unit (5) of the embodiment according to the invention of a weight measuring apparatus (1) illustrated in the previous figures.

FIG. 4.1 shows the configuration, also illustrated in FIG. 2, of an embodiment according to the invention of a weight measuring apparatus (1), in which the left-hand receiving and connecting device (6) is closed by a cover and the right-hand receiving and connecting device (6) is connected to a digital display and operator control unit (5).

In the step illustrated in FIG. 4.2, the cover has been removed from the left-hand receiving and connecting device (6).

FIG. 4.3 shows the embodiment according to the invention of a weight measuring apparatus (1) in a perspective view from the rear. A housing part (10) is releasably mounted on the rear of the housing of the top segment (4).

FIG. 4.4 shows the stand scale, illustrated in FIG. 4.3, from the rear, wherein the cover of the receiving and connecting device (6), the digital display and operator control unit (5), and the housing part (10) have been detached from the top segment (4). As a result of the detachable housing part (10) arranged at the rear, a position change of the digital display and operator control unit (5) is possible even in the case of the digital receiving and connecting device (5) being connected to the corresponding electronics of the rest of the weight measuring apparatus (1) by a cable, without the cable connection being released. In addition, a cable that connects the digital display and operator control unit (5) to the weight measuring apparatus (1) is concealed in the housing in both fully mounted positions of the display and operator control unit (5) in the region of the top segment (4).

FIG. 4.6 shows the embodiment according to the invention of a weight measuring apparatus (1) once the position change of the display and operator control unit (5) from the right-hand receiving and connecting device (6) to the left-hand receiving and connecting device (6) has been completed. The right-hand receiving and connecting device (6) is now closed by the cover.

Figure 5:
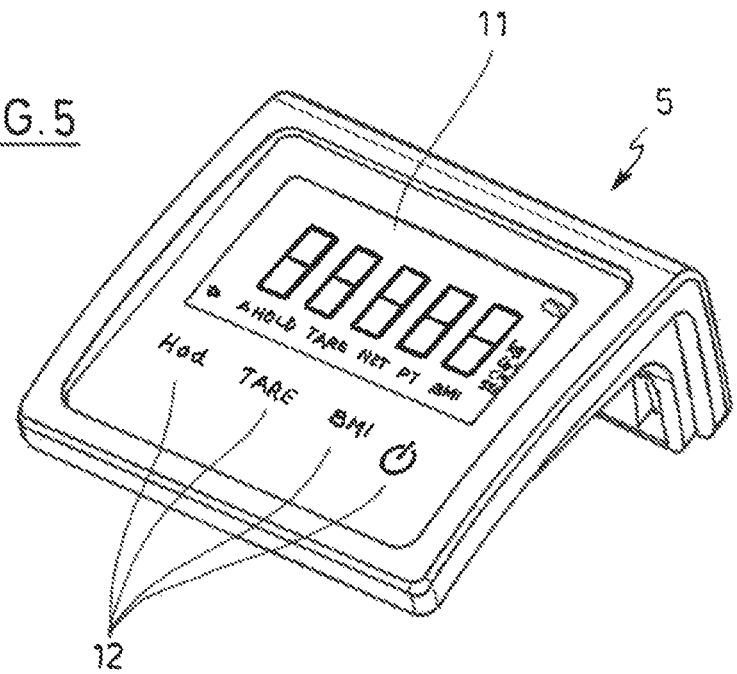
FIG. 5 shows a perspective view of a digital display and operator control unit configured according to the invention.

FIG. 5 illustrates an embodiment according to the invention of a digital display and operator control unit (5) of a weight measuring apparatus (1) in a perspective view. The digital display and operator control unit (5) has a display (11) and four input devices (12) arranged beneath the display (11). The input devices (12) are embodied as touch-sensitive touch elements. The display (11) has a segmented display for showing five digits for indicating recorded measurements. Furthermore, information about options selected by the operator and the charge state of a rechargeable battery integrated into the digital display and operator control unit (5) can be gathered from the display (11) of the digital display and operator control unit (5).

Figure 6:
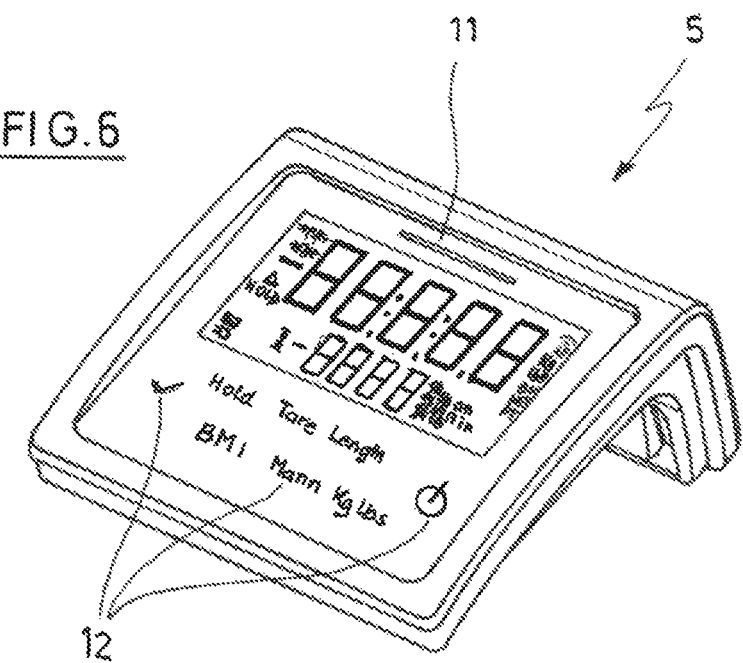
FIG. 6 shows a perspective view of a further digital display and operator control unit configured according to the invention, FIG. 7.1 shows a perspective view of an alternative embodiment of a weight measuring apparatus according to the invention with a movable control unit in a left position, FIG. 7.2 shows a view as in FIG. 7.1 with the control unit in a center position, and FIG. 7.3 shows a view as in FIG. 7.1 with the control unit in a right position.

FIG. 6 illustrates an embodiment of a digital display and operator control unit (5) of an embodiment according to the invention of a weight measuring apparatus (1) with expanded functionality. In addition to the weight measurement, a recorded height measurement is able to be shown. Furthermore, via additional input devices (12) a menu is able to be called up, a bio-impedance measurement is able to be started, a height measurement is able to be carried out, and a selection is able to be confirmed. Furthermore, the illustrated display and operator control unit (5) has a Wi-Fi interface, the connection status of which is able to be read from the display (11) of the display and operator control unit (5).

FIG. 7 shows, in FIGS. 7.1 to 7.3, three perspective illustrations of a further embodiment according to the invention of a weight measuring apparatus (1). The top segment (4) is in the form of a semicircular rail, on which a display and operator control unit (5) is movable in a stepless manner. As a result of the stepless movability, the top segment (4) has, along its extension, a multiplicity of receiving and connecting devices (6), or is, in its entirety, a single receiving and connecting device (6) with a de facto infinite number of positions at which the display and operator control unit (5) is functionally connectable thereto. The weight measuring apparatus (1) furthermore has three struts (3), which carry the top segment (4).

According to the illustration in FIG. 7.1, the display and operator control unit (5) is arranged in a region on the left-hand side of the top segment (4), in FIG. 7.2, the display and operator control unit (5) is arranged in a region at the center of the top segment (4), and in FIG. 7.3, the display and operator control unit (5) is arranged in a region on the right-hand side of the top segment (4).

As an alternative to the above-described embodiment of a weight measuring apparatus according to the invention in the form of a stand scale, embodiments with differing variants of the arrangement of struts and top segment as per the description are expressly also comprised.

While specific embodiments of the invention have been shown and described in detail to illustrate the inventive principles, it will be understood that the invention may be embodied otherwise without departing from such principles.

I claim:

1. A weight measuring apparatus, comprising: a base having a top side with a weighing surface; at least one strut extending upwardly from the base; a top segment mounted on the at least one strut and having a substantial horizontal extension component; at least one digital display and operator control unit arranged in a region of the top segment; and at least one receiving and connecting device arranged in the region of the top segment, the at least one digital display and operator control unit being connectable to the at least one receiving and connecting device so that the display and operator control unit is positionable in at least two different positions in the region of the top segment, wherein the at least one digital display and operator control unit is freely positionable within horizontal dimensions of the at least one receiving and connecting device.

2. The weight measuring apparatus according to claim 1, wherein the least one receiving and connecting device includes a receiving and connecting device in a left-hand region of the top segment and in a right-hand region of the top segment.

3. The weight measuring apparatus according to claim 1, wherein the at least one digital display and operator control unit is connectable to the at least one receiving and connecting device in at least two predetermined positions in the region of the top segment.

4. The weight measuring apparatus according to claim 1, further comprising electronics, wherein the at least one digital display and operator control unit is connectable by cable to the electronics.

5. The weight measuring apparatus according to claim 1, further comprising electronics, wherein the at least one digital display and operator control unit is connectable wirelessly to the electronics.

6. The weight measuring apparatus according to claim 1, wherein the at least one receiving and connecting device is arranged in the region of the top segment, said receiving and connecting device extending in a horizontal direction such that the at least one digital display and operator control unit is connectable to the receiving and connecting device in different positions.

7. A weight measuring apparatus, comprising: a base having a top side with a weighing surface; at least one strut extending upwardly from the base; a top segment mounted on the at least one strut and having a substantial horizontal extension component; at least one digital display and operator control unit arranged in a region of the top segment; and at least one receiving and connecting device arranged in the region of the top segment, the at least one digital display and operator control unit being connectable to the at least one receiving and connecting device so that the display and operator control unit is positionable in at least two different positions in the region of the top segment, wherein the at least one receiving and connecting device is a horizontally extending rail to which the at least one digital display and operator control unit is connectable.

8. A weight measuring apparatus, comprising: a base having a top side with a weighing surface; at least one strut extending upwardly from the base; a top segment mounted on the at least one strut and having a substantial horizontal extension component; at least one digital display and operator control unit arranged in a region of the top segment; and at least one receiving and connecting device arranged in the region of the top segment, the at least one digital display and operator control unit being connectable to the at least one receiving and connecting device so that the display and operator control unit is positionable in at least two different positions in the region of the top segment, wherein the at least one receiving and connecting device is a horizontally extending hook-and-loop strip.

9. A weight measuring apparatus, comprising: a base having a top side with a weighing surface; at least one strut extending upwardly from the base; a top segment mounted on the at least one strut and having a substantial horizontal extension component; at least one digital display and operator control unit arranged in a region of the top segment;

and at least one receiving and connecting device arranged in the region of the top segment, the at least one digital display and operator control unit being connectable to the at least one receiving and connecting device so that the display and operator control unit is positionable in at least two different positions in the region of the top segment, wherein the at least one receiving and connecting device is a horizontally extending magnetic or ferromagnetic element.

10. The weight measuring apparatus according to claim 1, further comprising a height measuring device.

11. The weight measuring apparatus according to claim 10, wherein the height measuring device is a height rod.

12. The weight measuring apparatus according to claim 10, wherein the height measuring device is vertically positionable.

13. The weight measuring apparatus according to claim 10, wherein the height measuring device has a head piece.

14. The weight measuring apparatus according to claim 1, wherein the weight measuring apparatus is a stand scale.

* * * * *